(12) United States Patent
Whitten

(10) Patent No.: US 6,394,258 B1
(45) Date of Patent: May 28, 2002

(54) APPARATUS FOR LOADING CONDOMS ONTO MANDRELS

(76) Inventor: James R. Whitten, P.O. Box 50096, Albany, GA (US) 31703

( * ) Notice: Subject to any disclaimer, the term of this patent is extended or adjusted under 35 U.S.C. 154(b) by 0 days.

(21) Appl. No.: 09/758,022

(22) Filed: Jan. 10, 2001

(51) Int. Cl.$^7$ ............................................... B65G 25/00
(52) U.S. Cl. ............... 198/468.2; 198/409; 198/750.11; 198/487.1; 414/225.01
(58) Field of Search ............................. 198/409, 487.1, 198/468.2, 750.11, 803.12; 414/751.1, 225.01, 908

(56) References Cited

U.S. PATENT DOCUMENTS

| | | | |
|---|---|---|---|
| 3,868,899 A | * 3/1975 | Nye et al. ............... | 198/803.12 |
| 3,983,809 A | * 10/1976 | Nye et al. ............... | 198/803.12 |
| 3,992,766 A | 11/1976 | Field | |
| RE30,410 E | 10/1980 | Povlacs | |
| 5,499,898 A | 3/1996 | Vonier et al. | |
| 5,564,552 A | 10/1996 | Vonier et al. | |

* cited by examiner

*Primary Examiner*—Joseph E. Valenza
(74) *Attorney, Agent, or Firm*—Thomas C. Saitta

(57) ABSTRACT

An apparatus for loading condoms onto mandrels is disclosed, the apparatus comprising a plural number of expansion rods adapted to receive and stretch a condom and a plural number of detaining rods to abut and retain the condom ring, the rods being mounted on a reciprocating carriage assembly which moves the rods past the mandrel, the mandrel itself stripping the condom from the rods.

16 Claims, 5 Drawing Sheets

APPARATUS FOR LOADING CONDOMS ONTO MANDRELS

BACKGROUND OF THE INVENTION

The invention relates generally to the field of apparatuses for loading condoms onto mandrels. More particularly, the invention relates to a condom loading apparatus utilizing a number of rods to expand the condom as it is placed onto the mandrel, where the apparatus is improved by providing a secondary set of rods to retain the ring of the condom while it is being loaded onto the mandrel.

The handling of condoms by mechanized means has long been a problem within the industry. Because condoms are elastic, non-rigid devices made of thin-walled latex or similar materials which maintain no particular shape or configuration unless supported from within or held by outside means, and because the condoms are very susceptible to tearing if mishandled, few devices have been developed which can successfully perform handling operations on condoms, such that most handling operations are by necessity carried out by hand. As an example of a common handling operation in condom manufacture, it is required that each condom be quality tested for the presence of minute holes after it is manufactured. This is commonly done by stretching each condom by hand onto a metal mandrel of appropriate shape. The condom is then passed over an electrically charged net and if any current passes from the net to the mandrel the condom is rejected, the completed circuit indicating that there is a hole in the insulating material forming the condom. The condoms which pass the test are then removed from the mandrel for packaging.

An apparatus for loading condoms onto mandrels is disclosed in U.S. Pat. No. 5,564,552, issued Oct. 16, 1996 to Vonier et al., and in U.S. Pat. No. 5,499,898, issued Mar. 19, 1996 to Vonier at al., the disclosures of both being incorporated herein by reference. The '898 patent discloses a complete testing apparatus which may comprise the condom loading apparatus disclosed in more detail in the '552 patent. The apparatus of the '552 patent comprises in general a mandrel loading means mounted onto a track, the loading means comprising a number of thin, elongated, generally parallel-oriented, expansion rods which occupy a relatively narrowin-diameter area in the passive position in order to receive a condom, but which can be expanded outwardly around the mandrel to expand the condom such that it can be positioned on the mandrel for subsequent testing. The configuration of the carriage and mount holding the expansion rods allows the carriage to be passed completely over the length of the mandrel and beyond into a recessed position with the expansion rods removed completely from the condom to allow subsequent movement of the loaded mandrel for testing purposes. The carriage is mounted onto a track such that it receives the condom from a condom retaining means at the uppermost portion of the track and is brought downward on a line such that the central longitudinal axis of the group of expansion rods is on the same line as the central longitudinal axis of a mandrel in the loading position. The mandrel itself forces the expansion rods outward in the radial direction, thereby stretching the condom to create an opening of sufficient size to receive the mandrel. There is sufficient friction between the condom and the expansion rods such that the condom loads onto the mandrel. The movement of the carriage down and past the mandrel removes the expansion rods from the condom, leaving the condom mounted on the mandrel. The mandrel can now be moved for testing and the carriage returned to the upper position. This cycle is then repeated for successive condoms.

It has been found that problems will often occur during the loading of the condom onto the mandrel due to variations in the elasticity of the condoms. This is typically a result of the age of the condoms, in that condoms freshly manufactured tend to be more elastic than older condoms, or may also be a result of manufacturing tolerances, ambient temperature variation or other reasons. During the loading operation, some condoms will not load completely onto the mandrel because they have lower than average elasticity, while some condoms may have higher than average elasticity, in which case they are pulled too far onto the mandrel. Since it is crucial in the testing operation for the condom to be properly loaded onto the mandrel, it is desirable to improve on the condom loading apparatus and methodology.

It is an object of this invention to provide an improved apparatus which can mechanically load a condom onto a mandrel. It is a further object of this invention to provide such an apparatus which utilizes expansion rods mounted on a movable carriage to stretch the condom onto the mandrel, whereby the condom is first positioned on the expansion rods in a passive state and the carriage is moved in a linear motion to expand the expansion rods radially to load the mandrel and then cleared into a retracted position, such that the loaded mandrel can then be moved for testing. It is a further object of this invention to provide such an apparatus which utilizes a secondary set of shorter detaining rods to detain the rolled ring at the base of a condom as it is being loaded onto a mandrel, wherein the detaining rods are expanded radially in conjunction with the expansion rods as the carriage is moved over the mandrel. These and other objects not specifically expressed at this point will become clear in the following description.

SUMMARY OF THE INVENTION

The invention comprises in general an improvement to a condom loading apparatus having mandrel loading means mounted onto a track, the loading means comprising a number of thin, elongated, parallel oriented, expansion rods disposed on a mount, where the expansion rods occupy a relatively restricted area of small diameter about a central longitudinal axis when in the passive position in order to receive a condom, but which can be expanded radially around the circumference of an elongated mandrel to stretch the condom onto the mandrel. The configuration of the carriage and mount holding the expansion rods allows the carriage to be passed over the length of the mandrel into a recessed position to allow subsequent movement of the loaded mandrel for testing purposes. The carriage is mounted onto a track such that it receives the condom onto the expansion rods in the passive configuration from a condom retaining means at the uppermost portion of the track and is brought downward on a line such that the central axis of the group of expansion rods is on the same line as the central axis of a mandrel in the loading position. The mandrel expands the expansion rods in the radial direction, thereby stretching the condom such that the condom is positioned onto the mandrel. The movement of the carriage down and past the mandrel strips the condom from the expansion rods onto the mandrel when the tip of the condom contacts the end of the mandrel, and the mandrel can now be moved for testing and the carriage returned to the upper position. This cycle is then repeated for successive condoms.

The improvement comprises means to grasp or detain the condom ring during the loading operation, the means comprising a set of detaining rods of significantly shorter length than the expansion rods, such that the detaining rods extend only a short distance into the condom. The free ends of the detaining rods are curved or hooked radially outward a short distance, or provided with a small protrusion. Like the expansion rods, the detaining rods occupy an area of small diameter in the passive state, but are expanded in the radial direction when drawn onto the mandrel. The outwardly extending detent ends of the detaining rods stretch the wall of the condom at a point above the rolled ring at the base of the condom, such that they temporarily retain the condom ring as the carriage is drawn onto the mandrel to prevent the condom from misleading. With the condom properly loaded on the mandrel, the detent ends retract into an annular recess on the mandrel body to release the condom ring.

DETAILED DESCRIPTION OF THE INVENTION

Figure 2:
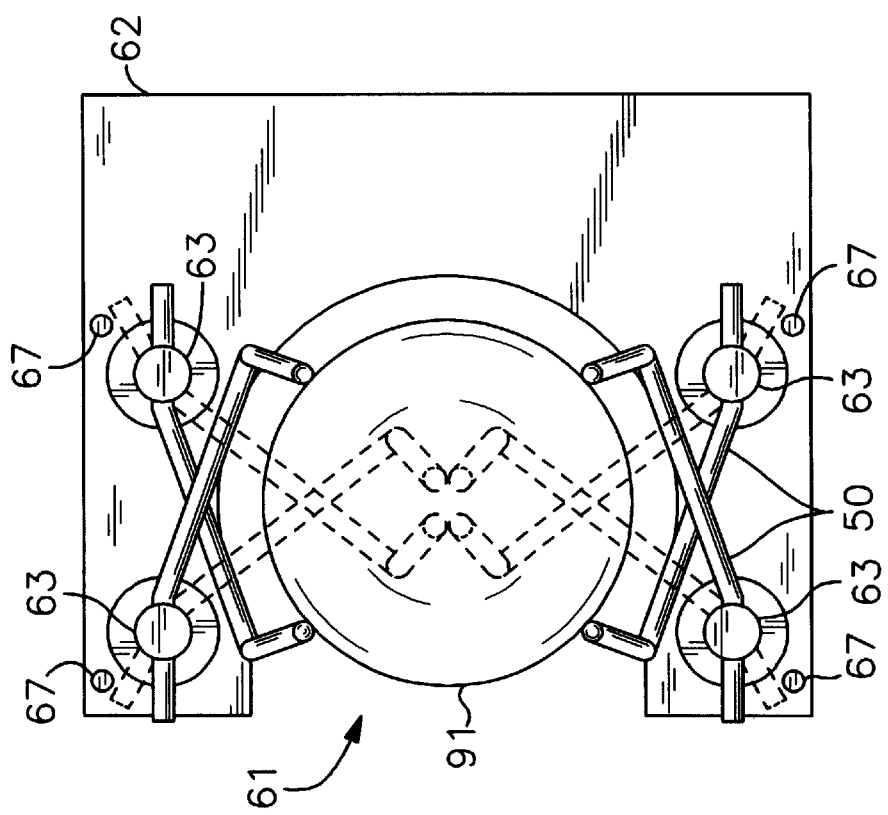
FIG. 2 is a view of prior art illustrating the initial receiving positioning of the expansion rods in outline and the subsequent expanded configuration about the mandrel.

With reference now to the drawings, the invention will be described in detail with regard to the best mode and preferred embodiment. The invention is an improvement to an apparatus for loading condoms 90 onto a mandrel 91 which is shaped to generally match the configuration of the condom 90, and comprises a movable carriage assembly 60 upon which are mounted a number of elongated expansion rods 50 for receiving and stretching a condom 90, whereby the condom 90 is deposited onto the mandrel 91 by movement of the carriage 60 relative to the mandrel 91 in the axial direction, or vice versa. The expansion rods 50 act as runners on the surface of the mandrel 91, such that there is no or at least greatly reduced resistance or contact between the mandrel 91 and the condom 60 until the tip of the condom 90 is brought down onto the tip of the mandrel 91. The improvement comprises the addition of a means 100 to detain or grasp the condom ring 99, and in particular comprises a plural number of shorter detaining rods 70, which act to detain the rolled ring 99 at the base of the condom 90 as the condom 90 is deposited onto the mandrel 91. An example of a prior art apparatus is fully disclosed in U.S. Pat. Nos. 5,564,552 and 5,499,898, and that disclosure is incorporated herein by reference. The improvement as discussed herein may also be applied to similar condom handling apparatuses not expressly described in those patents.

Figure 7:
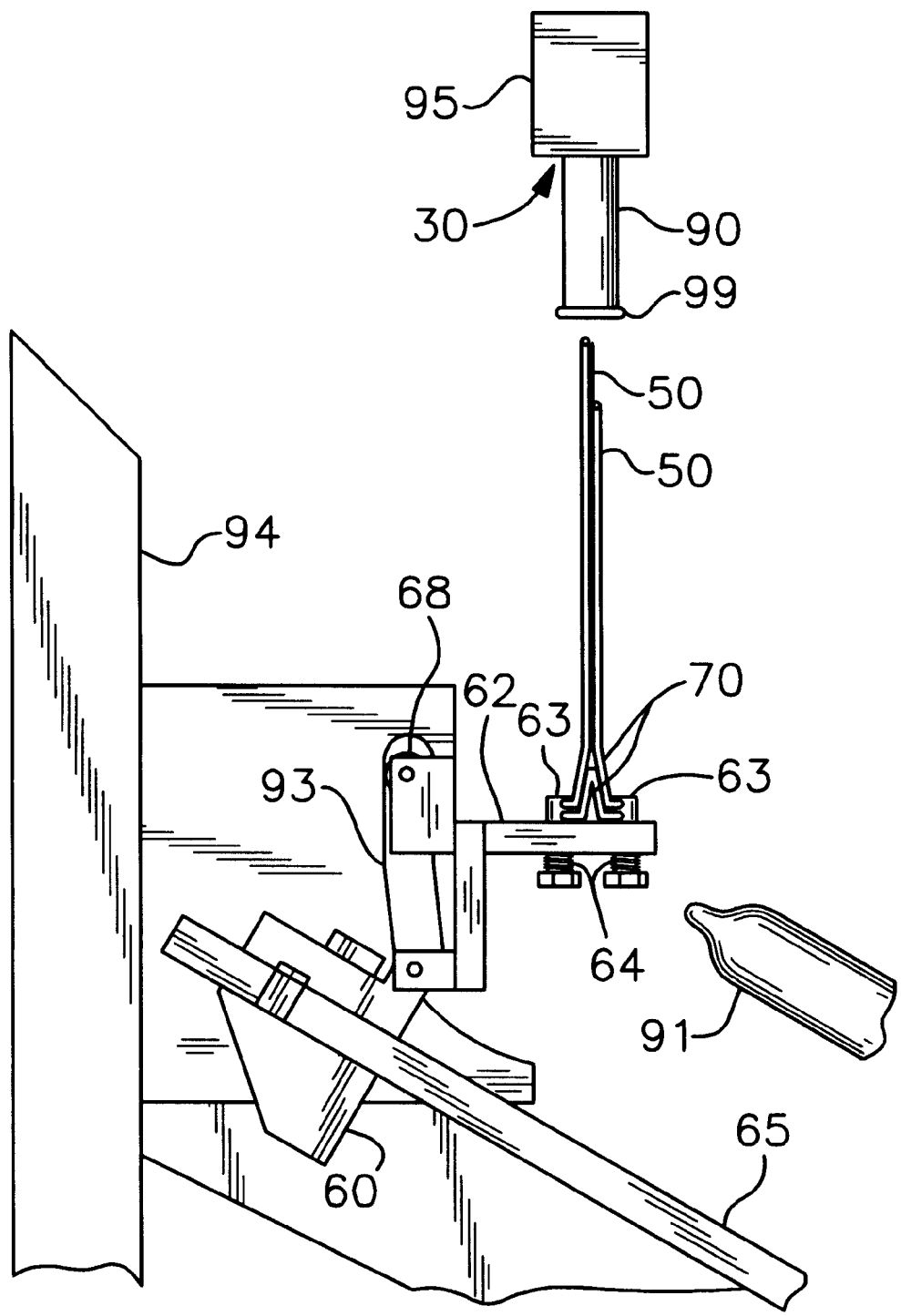
FIG. 7 is a view of the rod carriage with the rods in the passive receiving position.

The carriage assembly 60, expansion rods 50 and detaining rods 70 can be seen in FIG. 7 as particular components on a condom handling apparatus. This illustration shows the expansion rods 50 and receiving rods 70 disposed in the neutral or passive receiving position to receive the condom 90 prior to loading it onto the mandrel 91. The carriage assembly 60 is comprised of a rod mount 62 to which are attached the multiple expansion rods 50 and detaining rods 70. The carriage assembly 60 is mounted onto a linear carriage track 65 which allows reciprocal movement of the carriage 60 past the mandrel 91 to be loaded. Condom retaining means 95 holds the condom 90 in a vertical position with the tip of the condom 90 on top so that the base, ring 99 and open end of the condom 90 hang downward. Condom retaining means 95 can be any suitable mechanism for presenting the condom 90 in the described manner, and can comprise mechanical or suction means to hold the tip for release and to keep the body expanded to allow for insertion of the expansion rods 50 into the condom 90. Alternatively and preferably, it has been found that simply maintaining the tip of the condom 90 at the uppermost position and then releasing it to fall onto the expansion rods 50 is the simplest and most efficient way to place the condom 90 onto the expansion rods 50. As the condom 90 falls, air fills the interior through the open end, thus expanding the condom 90 like a parachute to settle onto the expansion rods 50.

Figure 1:
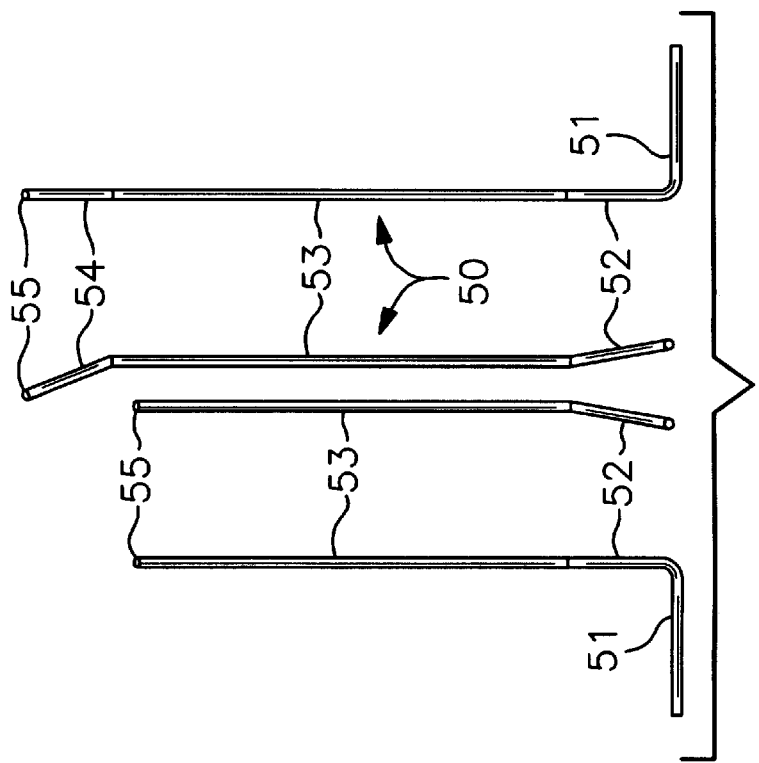
FIG. 1 is view of prior art showing a combination of front and side views of the expansion rod configurations.

Expansion rods 50 are preferably thin, elongated members of small cross-sectional diameter composed of a rigid metal or like material. While expansion rods 50 may be configured in many various shapes, the configuration shown in FIGS. 1 and 2 has been found to be very effective in loading the condom 90 onto the mandrel 91. It is best to use at least two expansion rods 50 to expand the condom 90 as it is drawn over the mandrel 91. The object is to minimize and or completely eliminate any contact between the sides of the mandrel 91 and the sides of the condom 90 during the loading step. The use of four expansion rods 50 positioned 90 degrees apart in the expanded configuration has been found to be highly efficient when no detaining rods 70 are present, but with the use of detaining rods 70 as described herein, it has been found that two expansion rods 50 alone will accomplish the task, as the detaining rods 70 overcome any increased friction effects between the mandrel 91 and the condom 90 due to the reduction in the number of expansion rods 50. The expansion rods 50 are pivotally mounted onto a generally U-shaped mount 62 surrounding a mandrel receiving opening 61. The connecting segment 51 of each expansion rod 50 is attached to a pivoting post 63, which is biased by a spring 64 such that the expansion rods 50 occupy a rest position, shown by the dotted lines in FIG. 2, with the tips 55 of all the expansion rods 50 being relatively contiguous or adjacent to one another and the main body segments 53 being generally parallel and also contiguous or adjacent each other. A positioning pin 67 is used to maintain the expansion rods 50 in this position. It is necessary that the tips 55 occupy a relatively small area so that they will not interfere with the drop of the condom 90, as the tip of the condom 90 should end up resting on the tips 55 of the expansion rods 50. In the preferred configuration, as seen in FIG. 1, each expansion rod 50 is comprised of a connecting segment 51 for insertion into the pivoting posts 63, a main body segment 53, a transition segment 52 joining the main body 53 and the connecting segment 51 angled such that the central axis of the main body segment 53 does not intersect the central axis of the connecting segment 51, and a blunt or rounded tip 55. Preferably, one expansion rod 50 is slightly longer than the others and is provided with a centering extension segment 54, whereby the tip 55 of this expansion rod 50 is positioned on the central axis of the grouping of all the expansion rods 50. This results in only a single uppermost tip 55, thus insuring that the condom 90 will not be snagged as it is dropped onto the expansion rods 50. This configuration is preferred as it enables the main body segment 53 of each expansion rod 50 to remain parallel to the sides of the mandrel 91 as they are passed down over it.

Figure 3:
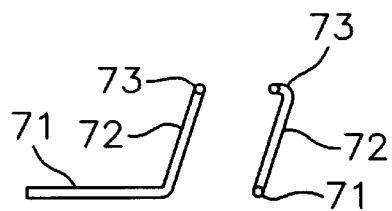
FIG. 3 is a view showing a combination of front and side views of the detaining rod configurations.
Figure 4:
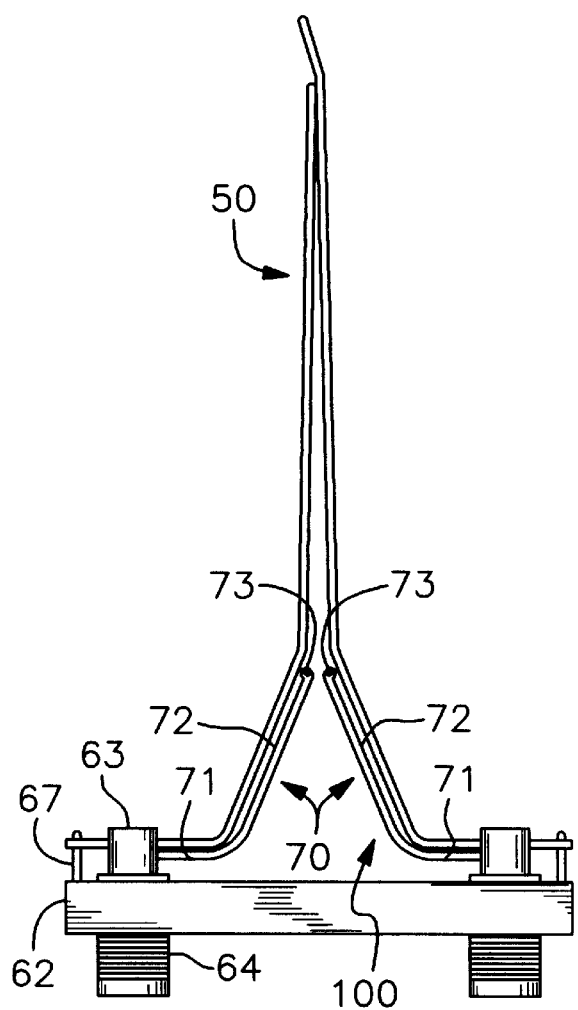
FIG. 4 is a side view of the carriage with the rods in the passive configuration.
Figure 5:
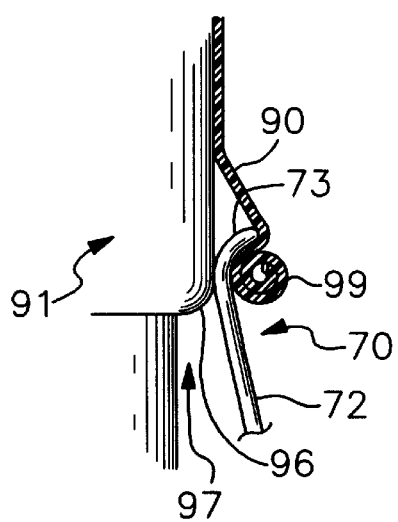
FIG. 5 is a partial view of the detaining rods in contact with the condom ring.
Figure 6:
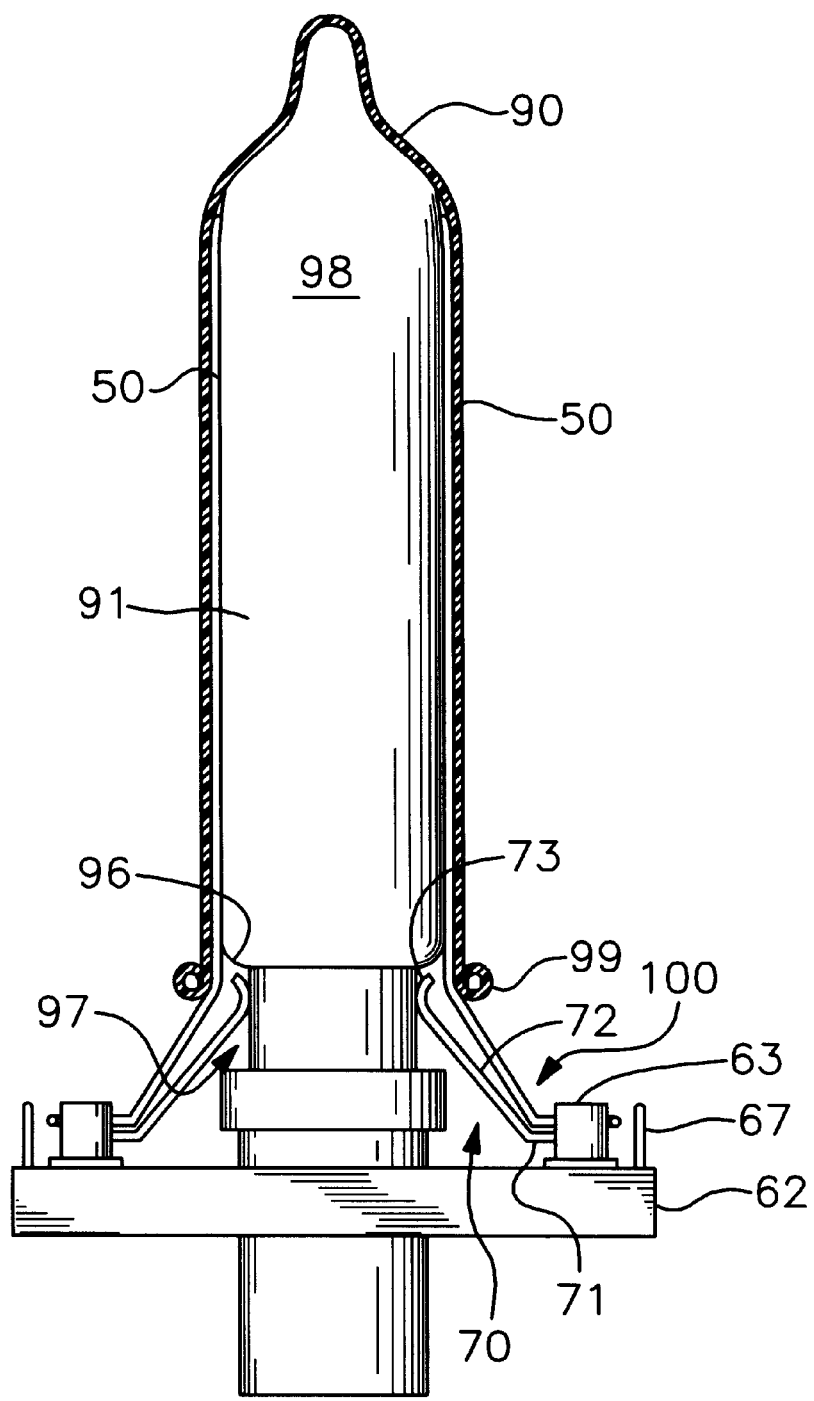
FIG. 6 is a side view of the carriage disposed about a mandrel, with the condom released from the detaining rods.

The detaining rods 70 are best seen in FIGS. 4 through 6. The detaining rods 70 are preferably short, thin, elongated members of small cross-sectional diameter composed of a rigid metal or like material. While detaining rods 70 may be configured in many various shapes, the configuration shown in FIG. 3 has been found to be very effective in retaining the condom ring 99 as the condom 90 is loaded onto the mandrel 91. It is best to use a plural number, and preferably at least two up to four or more, detaining rods 70 to grasp the condom 90 as it is drawn over the mandrel 91. The use of four detaining rods 70 positioned 90 degrees apart in the expanded configuration is shown in the drawings. The detaining rods 70 are preferably pivotally mounted onto the generally U-shaped mount 62 within the pivoting posts 63 which retain the expansion rods 50. The detaining rods 70 each comprise a connecting segment 71 mounted in the pivoting post 63, an angled transition segment 72 and a detent end 73 which is formed in the shape of a hook, ball, curved segment or other short protrusion. Alternatively, the detaining rods 70 may be separately mounted onto the U-shaped mount 62 apart from the expansion rods 50, which may be required when the number of detaining rods 70 and the number of expansion rods 50 are not equal.

In the passive state prior to the carriage assembly 60 being moved onto the mandrel 91, the detent ends 73 and transition segments 72 of the detaining rods 70 occupy a centralized axial position of relatively small area within the bounds of the area formed by the expansion rods 50, as shown in FIG. 4. This allows the condom 90 to fall onto the expansion rods 50 unimpeded by the detaining rods 70, with the condom ring 99 resting below the detent ends 73 of the detaining rods 70. As the carriage assembly 60 is brought onto and over the mandrel 90, the mandrel 90 forces the expansion rods 50 and the detaining rods 70 outward in the radial direction due to rotation of the pivoting posts 63. The detent ends 73 of the detaining rods 70 extend radially from transition segment 72 in the expanded configuration, such that the detent ends 73 press out the wall of the condom 90, as shown in FIG. 5. The detent ends 73 abut the condom 90 above the condom ring 99, thereby retaining the ring 99 against movement in the axial direction toward the tip of the condom 90. As the carriage assembly 60 reaches the fully loaded position where the condom 90 is correctly positioned on the mandrel 90, the transition segments 72 and detent ends 73 of the detaining rods 70 encounter a shoulder 96 on mandrel 90 which defines a recess 97 of lesser outer diameter than the main body 98 of mandrel 90, as shown in FIG. 6. As the carriage assembly 60 continues in relative motion to the mandrel 90, the detent ends 73 retract into the recess 97 such that the detent ends 73 occupy a smaller circumferential area and no longer contact and detain condom ring 99.

Figure 8:
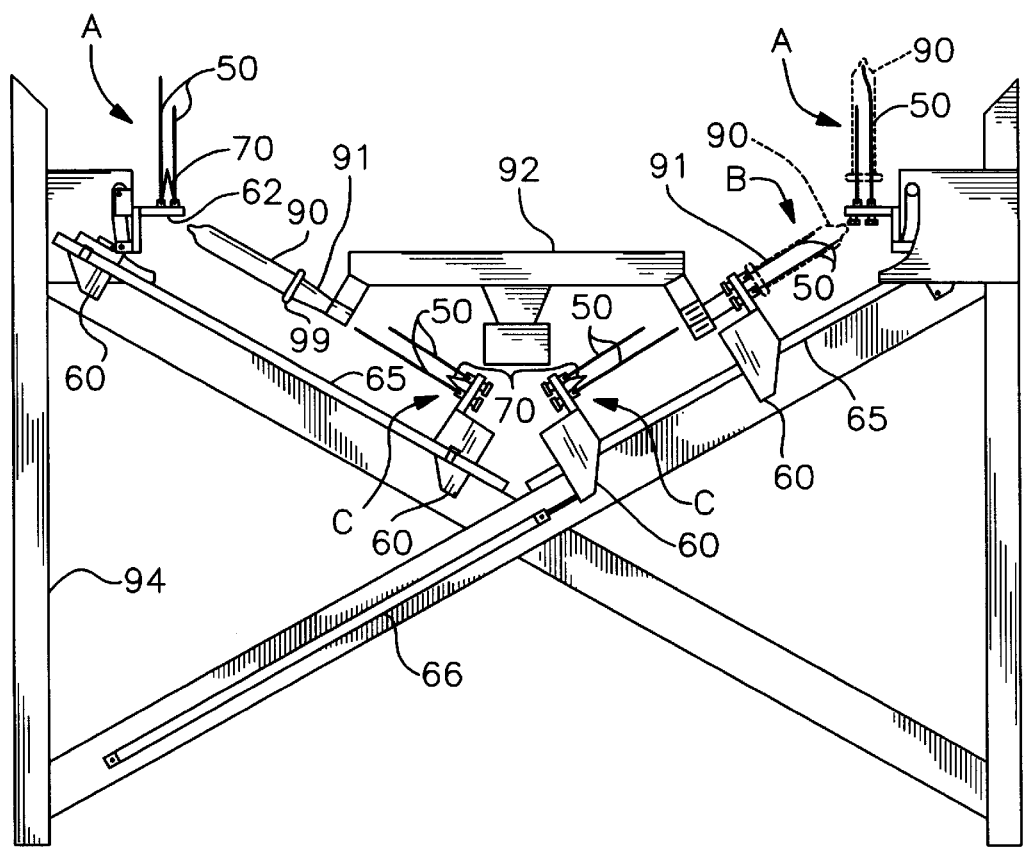
FIG. 8 is a view of the loading apparatus showing rod carriages in various positions of the loading cycle.

FIG. 8 shows an apparatus with two carriage tracks 65. A reciprocating means 66, such as an air cylinder, mounted onto a frame 94 moves each carriage 60 up and down track 65. Three positions A, B and C are illustrated. Position A is the receiving position previously described at which the condom 90 is placed onto the expansion rods 50. Position B is the mandrel loading position, and position C is the retracted carriage position. After the condom 90 is placed onto the rods 50 and 70, the carriage assembly 60 is moved down along track 65 to mandrel 91. The mandrel receiving opening 61 is positioned so as to be exposed relative to the carriage 60 and the track 65, in the upward orientation as shown. The mandrel 91 is mounted so as to depend generally laterally from a mandrel shuttle 92. As the carriage assembly 60 is brought down to mandrel 91, it freely passes over the mandrel 91 because of the mandrel receiving opening 61. As the tip of the mandrel 91 encounters the transition segments 52 and 72 of the expansion rods 50 and detaining rods 70, they are forced outward in the radial direction. This stretches the condom 90 to a size greater than the outer circumference of the mandrel 91, the main body segments 53 of the rods 50 acting as runners and spacers along the length of the mandrel 91, and the detent ends 73 of the detaining rods securing the condom ring 99 against axial movement toward the tip of the mandrel 91. As the carriage 60 is brought lower, the tip of the mandrel 91 encounters the tip of the condom 90 and acts as an anchor, as shown in position B of FIG. 8, so that the condom 90 is fully disposed onto the mandrel 91. The carriage 60 continues downward, the detaining rods 70 retract into the recessed position, and the expansion rods 50 and detaining rods 70 are pulled out of the condom 90, leaving the condom 90 fully loaded onto the mandrel 91. With the carriage 60 now in the fully retracted position C, the mandrel shuttle 92 can move the loaded mandrel 91 to the testing and then the condom removal position. When mandrel 91 is moved away from track 65, the carriage 60 is returned to the receiving position A for another cycle.

As explained, it is preferable that the rods 50 and 70 be in a vertical position to receive the condom 90, especially when the gravity drop method is utilized. For removal of the condom 90 from the mandrel 91 after testing in the embodiment as shown, it is preferred that the mandrel 91 be non-vertically oriented. As shown in FIG. 4, this requires that the expansion rods 50 and 70 be repositioned from the vertical alignment of position A to the alignment of position B which matches the mandrel 91 alignment. In this embodiment, this realignment is accomplished by pivotally attaching the rod mount 62 to carriage 60 and positioning a roller 68 which enters an orienting slot 93 on frame 94 at the upper end of track 65, as seen in FIG. 7. As carriage assembly 60 is moved upward by reciprocating means 66, the roller 68 pivots the mount 62 such that the rods 50 and 70 are vertically aligned. As the carriage 60 is lowered, the mount 62 pivots back into its resting position and the rods 50 and 70 are aligned with mandrel 91.

It is understood that equivalents and substitutions to elements or components set forth above may be obvious to those skilled in the art. The full scope and definition of the invention therefore is to be as set forth in the following claims.

I claim:

1. In an apparatus for loading a condom onto a mandrel, said apparatus comprising a carriage assembly comprising a plural number of expansion rods attached to a mount, said expansion rods each comprising a main body segment and tip, whereby said main body segments and said tips of said rods are positioned adjacent each other in a passive position to receive a condom having a condom ring, and are adapted to be expanded outward by passing said carriage assembly over a mandrel such that said rods expand said condom to a size greater than said mandrel, said carriage assembly being adapted to pass completely over said mandrel such that said mandrel removes said condom from said expansion rods and said condom is retained on said mandrel, the improvement comprising a plural number of detaining rods attached to said mount, said detaining rods being shorter than said expansion rods, and said detaining rods each comprising a detent end, whereby said detent ends occupy a passive position of small area to receive said condom, but are expanded outward by said mandrel as said carriage assembly is passed over said mandrel such that said detent ends abut and retain said condom ring during loading of the condom onto the mandrel.

2. The apparatus of claim 1, where said mandrel further comprises a recess to receive said detent ends upon said condom being fully loaded onto said mandrel, such that said detent ends retract inwardly and no longer abut and retain said condom ring when said condom is removed from said expansion rods.

3. The apparatus of claim 1, where said detent ends comprise a curved segment.

4. The apparatus of claim 1, where said detaining rods are pivotally connected to said mount.

5. The apparatus of claim 1 where said detaining rods each further comprise a transition segment, such that said mandrel contacts said transition segment to expand said detaining rods when said carriage assembly is passed over said mandrel.

6. An apparatus for loading a condom having a condom ring onto a mandrel, said apparatus comprising a mount, elongated expansion rods connected to said mount, whereby said expansion rods are disposed relatively adjacent each other in a passive state to receive a condom and are adapted to expand outward to receive a mandrel, and means for retaining said condom ring of said condom during the loading of said condom onto said mandrel.

7. The apparatus of claim 6, wherein said condom ring retaining means comprises detaining rods connected to said mount, said detaining rods being shorter than said expansion rods, whereby said detaining rods are adapted to expand outward during the loading of said condom onto said mandrel to retain the condom ring of said condom disposed onto said expansion rods.

8. The apparatus of claim 7, wherein said detaining rods each have a detent end which contacts said condom when said detaining rods are disposed in an expanded configuration.

9. The apparatus of claim 7, wherein said detaining rods are pivotally connected to said mount.

10. The apparatus of claim 9, wherein said expansion rods are pivotally connected to said mount.

11. In an apparatus for loading a condom onto a mandrel, said apparatus comprising in combination a carriage assembly and a mandrel, said carriage assembly comprising a plural number of expansion rods attached to a mount, said expansion rods adapted to be disposed adjacent each other in a passive position to receive a condom having a condom ring, and adapted to be expanded outward by passing said carriage assembly over said mandrel such that said expansion rods expand said condom to a size greater than said mandrel, said carriage assembly being adapted to pass completely over said mandrel such that said mandrel removes said condom from said expansion rods and said condom is retained on said mandrel, the improvement comprising means to retain said condom ring when said condom is loaded onto said mandrel.

12. The apparatus of claim 11, wherein said condom ring retaining means comprises a plural number of detaining rods attached to said mount, said detaining rods being shorter than said expansion rods, and said detaining rods each comprising a detent end, whereby said detent ends are adapted to be expanded outward by said mandrel as said carriage assembly is passed over said mandrel such that said detent ends abut and retain said condom ring during loading of said condom onto said mandrel.

13. The apparatus of claim 12, wherein said detent ends are further adapted to be disposed within said expansion rods in said passive position.

14. The apparatus of claim 13, wherein said expansion rods and said detaining rods are pivotally connected to said mount.

15. The apparatus of claim 12, wherein said mandrel further comprises a recess to receive said detent ends upon said condom being fully loaded onto said mandrel, such that said detent ends retract inwardly and no longer abut and retain said condom ring when said condom is removed from said expansion rods.

16. The apparatus of claim 12, wherein said detaining rods each further comprise a transition segment, such that said mandrel contacts said transition segment to expand said detaining rods when said carriage assembly is passed over said mandrel.

\* \* \* \* \*